(12) United States Patent
Bauer et al.

(10) Patent No.: US 8,224,440 B2
(45) Date of Patent: Jul. 17, 2012

(54) ELECTRICALLY ISOLATING ELECTRICAL COMPONENTS IN A MEDICAL ELECTRICAL LEAD WITH AN ACTIVE FIXATION ELECTRODE

(75) Inventors: Ryan Thomas Bauer, Plymouth, MN (US); Scott Brainard, Columbia Heights, MN (US); Lawrence M. Kane, Roseville, MN (US); Warren S. Dabney, Orchard Park, NY (US); Robert Shawn Johnson, North Tonawanda, NY (US); Robert A. Stevenson, Canyon Country, CA (US); Holly Noelle Moschiano, Lancaster, NY (US)

(73) Assignee: Greatbatch Ltd., Clarence, NY (US)

( * ) Notice: Subject to any disclaimer, the term of this patent is extended or adjusted under 35 U.S.C. 154(b) by 100 days.

(21) Appl. No.: 12/873,862

(22) Filed: Sep. 1, 2010

(65) Prior Publication Data
US 2010/0324640 A1    Dec. 23, 2010

Related U.S. Application Data

(63) Continuation-in-part of application No. 12/607,234, filed on Oct. 28, 2009, now Pat. No. 8,175,700, and a continuation-in-part of application No. 11/943,854, filed on Nov. 21, 2007, now Pat. No. 7,853,325, which is a continuation-in-part of application No. 11/558,349, filed on Nov. 9, 2006, now Pat. No. 7,945,322.

(60) Provisional application No. 61/314,676, filed on Mar. 17, 2010, provisional application No. 61/245,720, filed on Sep. 25, 2009, provisional application No. 61/243,643, filed on Sep. 18, 2009.

(51) Int. Cl.
*A61N 1/00* (2006.01)
(52) U.S. Cl. .......................................................... 607/2
(58) Field of Classification Search ........................ 607/2
See application file for complete search history.

(56) References Cited

U.S. PATENT DOCUMENTS

| 5,531,780 | A * | 7/1996 | Vachon ........................ 607/120 |
| 6,944,489 | B2 | 9/2005 | Zeijlemaker et al. |
| 7,363,090 | B2 | 4/2008 | Halperin et al. |
| 7,535,693 | B2 | 5/2009 | Stevenson et al. |
| 2007/0112398 | A1 | 5/2007 | Stevenson et al. |
| 2010/0100164 | A1 | 4/2010 | Johnson et al. |
| 2010/0324640 | A1 | 12/2010 | Bauer et al. |

* cited by examiner

*Primary Examiner* — George Manuel
(74) *Attorney, Agent, or Firm* — Kelly & Kelley, LLP; Michael F. Scalise

(57) ABSTRACT

A lead body adapted for in-vivo implantation in a living subject includes a proximal end configured for electrical and mechanical connection to a therapy or a monitoring device, and a distal end. A collar is disposed at the distal end of the lead body, and a casing is disposed within the collar and is translatable along a central longitudinal axis of the collar. At least one electrical conductor extends substantially the length of the lead body, and an electronic component is disposed within the casing and conductively coupled to the electrical conductor. An electrode is mechanically connected to the casing and conductively coupled to the electronic component. A seal is disposed between the casing assembly and the collar to prevent passage of ionic fluid into the lead body through its distal end.

38 Claims, 11 Drawing Sheets

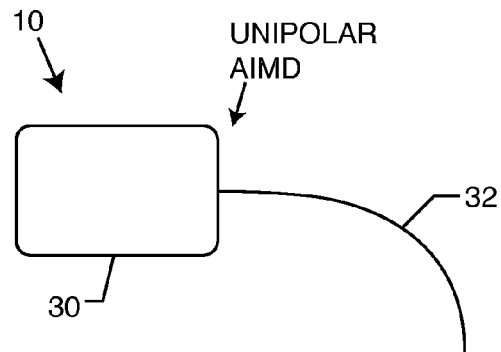
FIG. 4
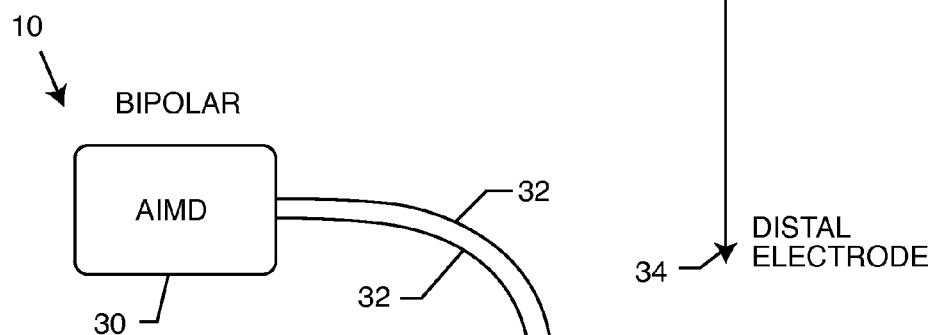
FIG. 5
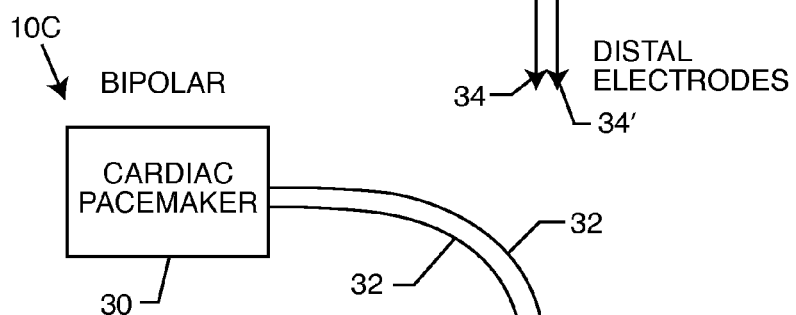
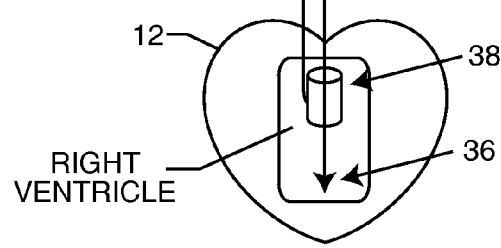
FIG. 6

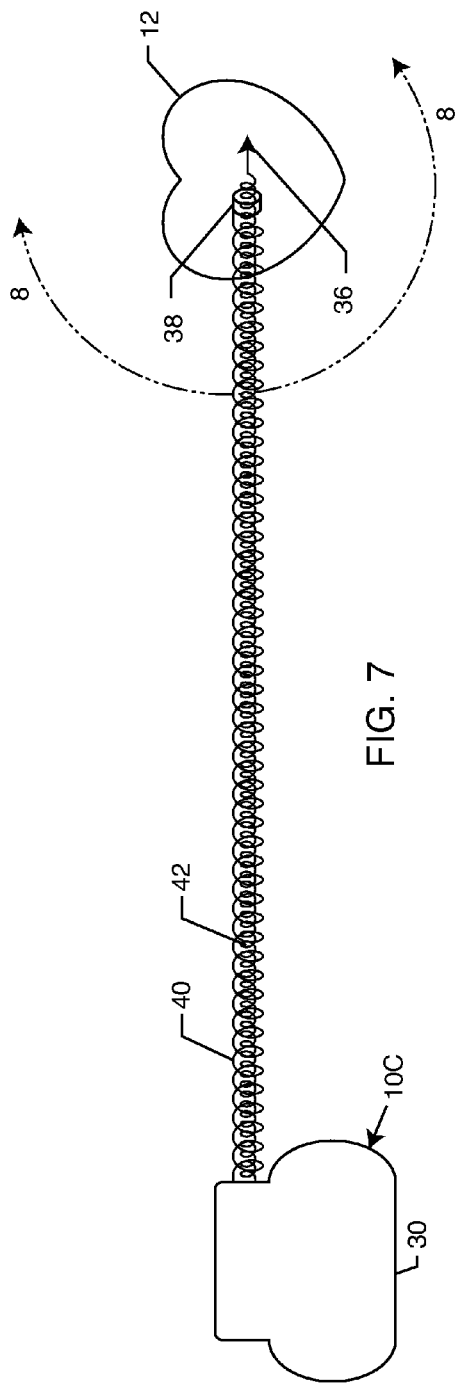
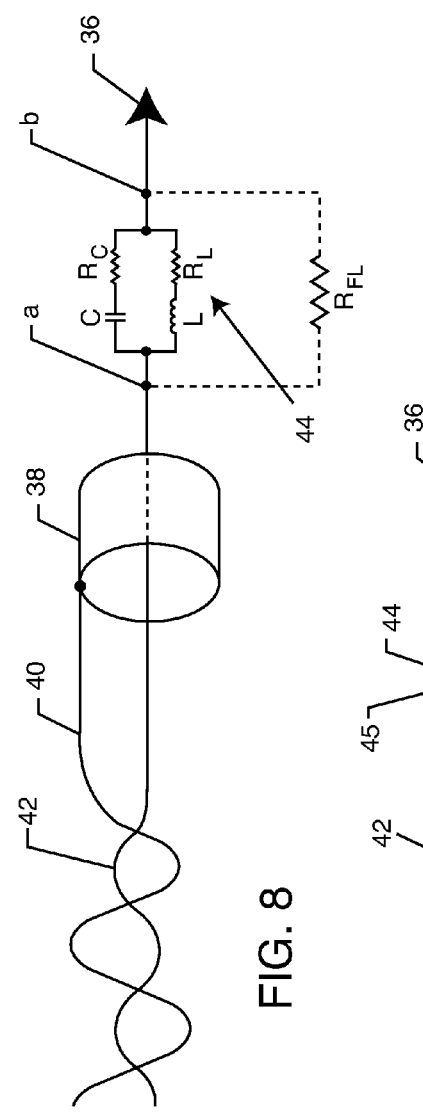
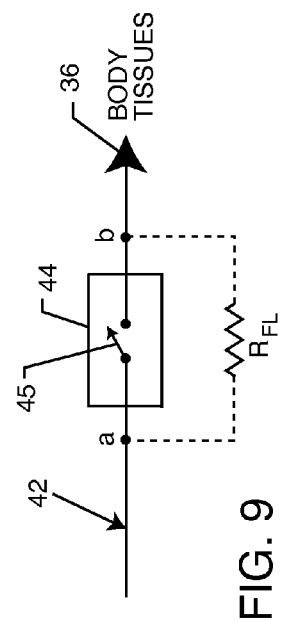
FIG. 7
FIG. 8
FIG. 9

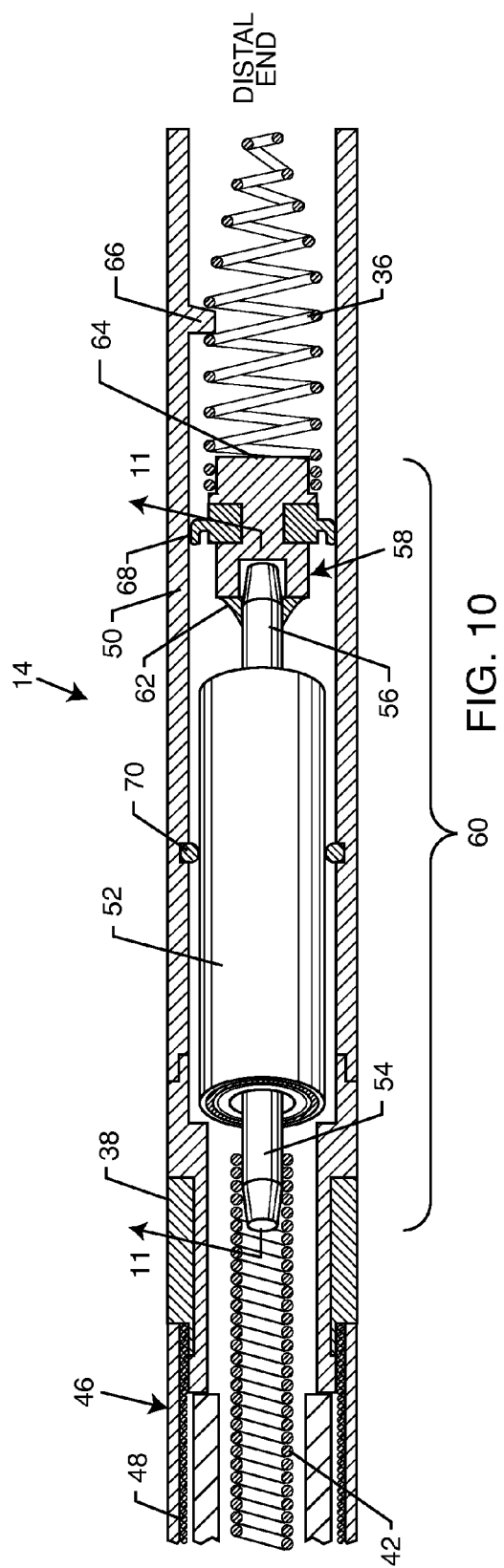
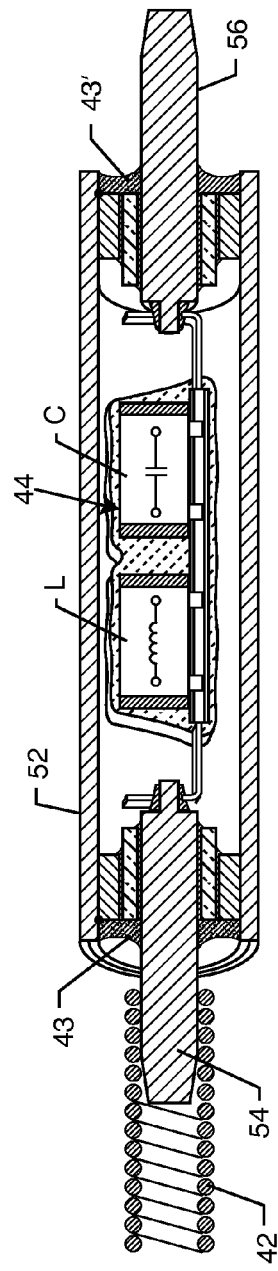
FIG. 10
FIG. 11

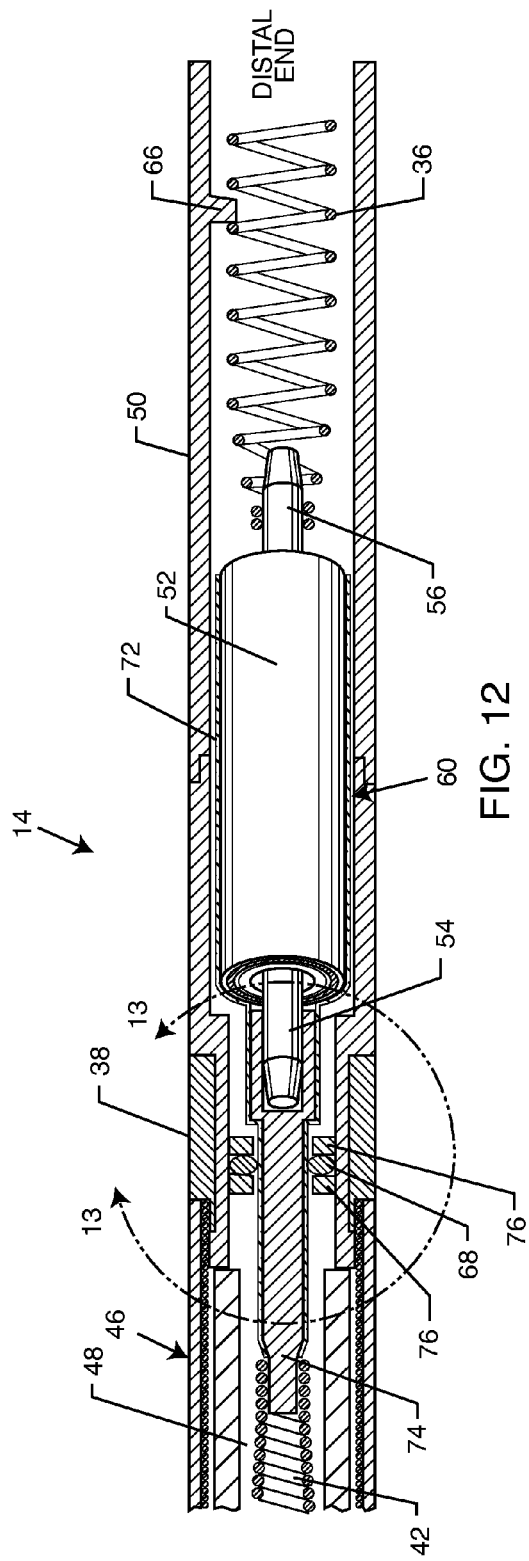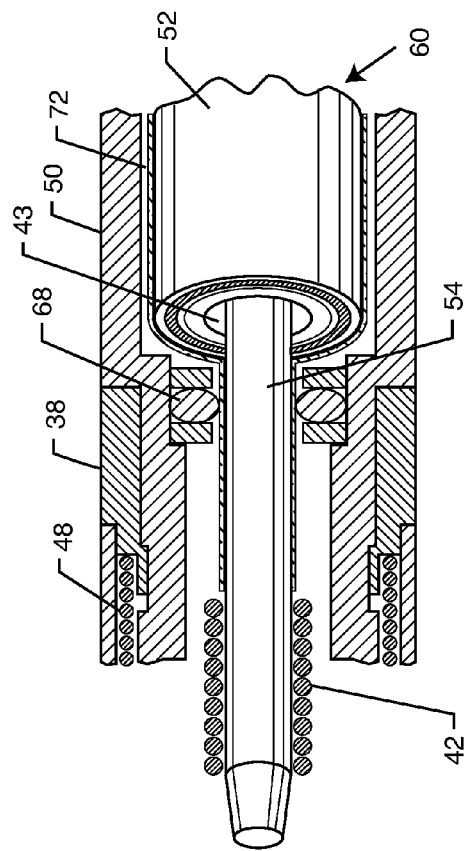

ELECTRICALLY ISOLATING ELECTRICAL COMPONENTS IN A MEDICAL ELECTRICAL LEAD WITH AN ACTIVE FIXATION ELECTRODE

FIELD OF THE INVENTION

The present invention generally relates to implantable medical electrical leads. More particularly, the present invention relates to a lead body adapted for in-vivo implantation in a living subject.

BACKGROUND OF THE INVENTION

A wide assortment of implantable medical devices are presently known and in commercial use. Such devices include cardiac pacemakers, cardiac defibrillators, cardioverters, neurostimulators, and other devices for delivering and/or receiving electrical signals to/from a portion of the body. Sensing and/or stimulating leads extend from the associated implantable medical device to a distal tip electrode or electrodes in contact with body tissue. These electrodes should be securely fixed to the tissue to facilitate electrical stimulation or sensing by the implantable medical device.

In order to work reliably, leads need to be stably located adjacent to the tissue to be stimulated or monitored. One common mechanism for accomplishing this has been the use of a fixation helix, which exits the distal end of the lead and is screwed directly into the body tissue. The helix itself may serve as an electrode or it may serve as an anchoring mechanism to fix the position of an electrode mounted to or forming a portion of the lead itself. This is known in the art as active fixation.

One problem associated with implanted leads is that they act as an antenna and tend to pick up stray electromagnetic signals from the surrounding environment. This is particularly problematic in an MRI environment where the currents which are imposed on the leads can cause the leads to heat to the point where tissue damage is likely. Moreover, the currents developed in the leads during an MRI procedure can damage the sensitive electronics within the implantable medical device. Bandstop filters, such as those described in U.S. Pat. No. 7,363,090 and U.S. 2007/0112398 A1, which are herein incorporated by reference, reduce or eliminate the transmission of damaging frequencies along the leads while allowing the desired frequencies to pass efficiently through.

Accordingly, there is a need for housing and electrically isolating electrical components in a medical electrical lead. The present invention fulfills these needs and provides other benefits.

SUMMARY OF THE INVENTION

The implantable medical lead of the present invention includes a lead body adapted for in-vivo implantation in a living subject. The lead body includes a proximal end configured for electrical and mechanical connection to a therapy delivery and/or a monitoring device, and a distal end active fixation electrode assembly. A collar is disposed at the distal end of the lead body. A casing is disposed within the collar and is translatable along a longitudinal axis of the collar. At least one electrical conductor extends substantially the length of the lead body. At least one electronic component is disposed within the casing and conductively coupled to the electrical conductor. In a preferred embodiment, the casing is hermetically sealed. The electronic component(s) may be either an active component(s) or a passive component(s). An electrode is mechanically connected to the casing and conductively coupled to the electronic component. In the preferred embodiment, a seal is disposed between the casing and the collar to prevent passage of ionic fluid from the living subject into the lead body through its distal end.

The seal may be disposed at a distal end of the casing, at a proximal end of the casing, or even along a middle of the casing. Furthermore, the seal may be fixed relative to the casing or the collar. The electrical component may comprise a bandstop filter or other electronic circuits such as electronic switches. The seal prevents ingress of bodily fluids inside the lead body and electrically isolates the electronic component and the pins of the casing. Isolating the pins extending in non-conductive relationship with the casing from each other is very important. For example, a bandstop filter may present an impedance of 2000 ohms at resonance. This desirably impedes the flow of MRI induced RF current into body tissue through the electrode. However, if the pins are not isolated from each other, a parallel path through body fluids (ionic fluid) could result in a parallel path of approximately 80 ohms. This conduction through surrounding fluid would degrade the MRI RF signal attenuation. Accordingly, it's very important to be able to isolate the opposite ends of the pins of the electronic component.

An insulative and dielectric conformal coating may be disposed about a portion of the casing, the inner surface of the collar, a portion of the electrical conductor, or any combination thereof. The conformal coating may be comprised of a biocompatible dielectric material such as alumina or parylene that is applied by sputtering, chemical vapor deposition, physical vapor deposition, or chemical dip. The casing may include a distal pin and a proximal pin, where the electrical conductor is attached to the proximal pin and the electrode is attached to the distal pin. The insulative conformal coating may be disposed about the proximal pin such that the proximal and distal pins are electrically insulated when surrounded by an ionized fluid, such as body fluids. The casing itself may also be comprised of a dielectric ceramic tube material such as alumina.

The seal may comprise a plurality of seals, multiple wipers, o-rings, thin disks, or thin sheets. Further, the seal may comprise a non-conductive bellows attached between the collar and the casing. The bellows may be expandable and collapsible and pre-spiraled in a collapsible configuration.

Further, a drive shaft is usually associated with a distal end of the at least one electrical connector. The drive shaft may comprise a hollow stylet-receiving rigid tube that surrounds at least a portion of the distal end of the electrical connector.

Other features and advantages of the present invention will become apparent from the following more detailed description which illustrate, by way of example, the principles of the invention.

BRIEF DESCRIPTION OF THE DRAWINGS

The accompanying drawings illustrate the invention. In such drawings:

FIG. 4 is a schematic diagram of a unipolar active implantable medical device;

FIG. 5 is a diagram similar to FIG. 4, illustrating a bipolar active implantable medical device;

FIG. 6 is a diagram similar to FIGS. 4 and 5, illustrating a biopolar lead wire system with a tip and ring electrode, typically used in a cardiac pacemaker;

FIG. 7 illustrates a bipolar cardiac pacemaker lead wire showing the tip and ring electrodes;

FIG. 8 is an enlarged, fragmented schematic illustration of the area illustrated by the line 8-8 in FIG. 7;

FIG. 9 is a schematic illustration similar to FIG. 8, showing the undesirability of permitting a parallel electrical path through body fluids around an impeding electrical component;

FIG. 10 is a sectional view of an exemplary medical electrical lead embodying the present invention;

FIG. 11 is an enlarged sectional view of the area illustrated by the line 11-11 in FIG. 10;

FIG. 12 is another sectional view of an exemplary medical lead, similar to FIG. 10, embodying the present invention;

FIG. 13 is an enlarged sectional view of the area illustrated by the line 13-13 in FIG. 12, showing an alternate configuration;

DETAILED DESCRIPTION OF THE PREFERRED EMBODIMENTS

Figure 1:
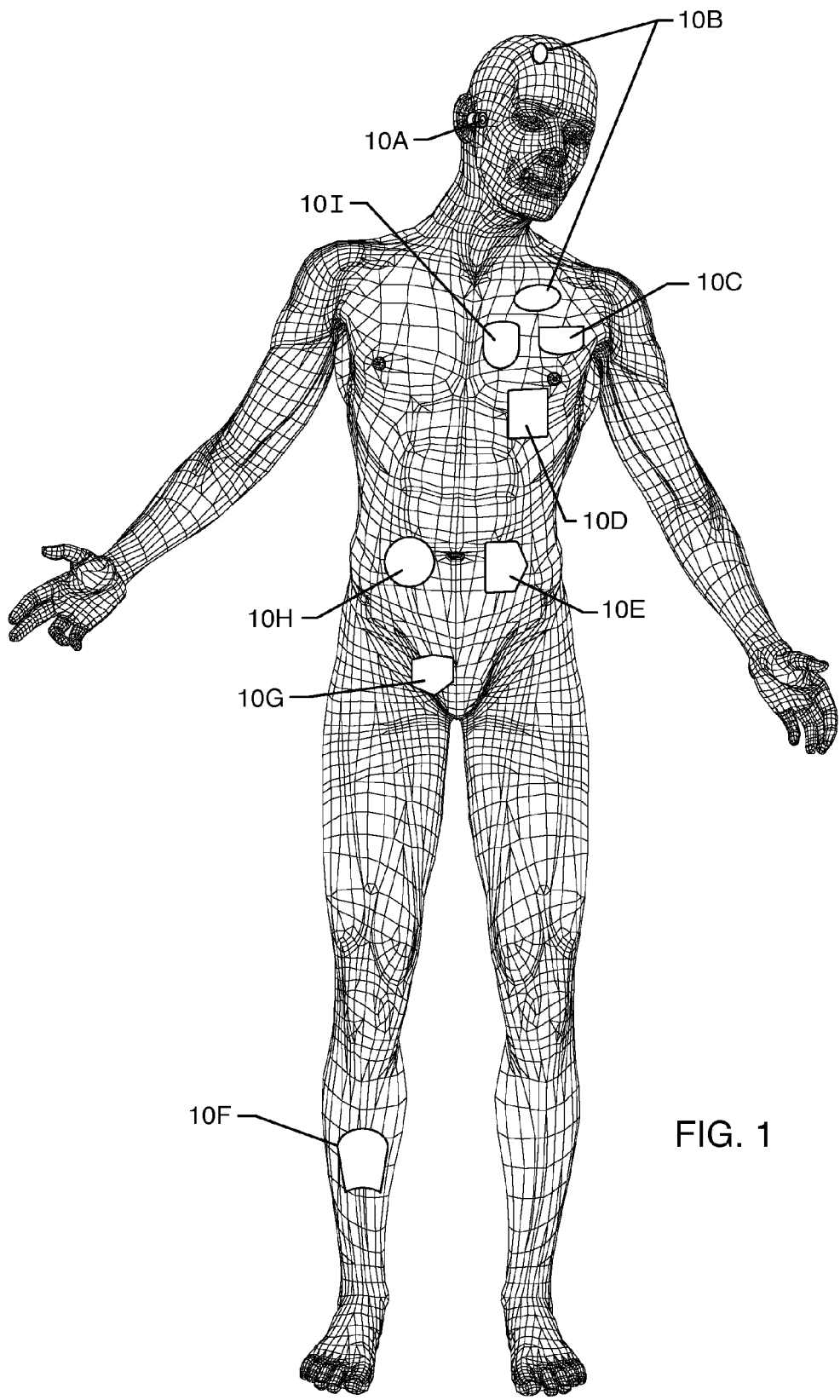
FIG. 1 is a wire-formed diagram of a generic human body showing a number of exemplary implanted medical devices.

FIG. 1 is a wire formed diagram of a generic human body showing a number of implanted medical devices. 10A represents a family of hearing devices which can include the group of cochlear implants, piezoelectric sound bridge transducers and the like. 10B represents a variety of neurostimulators and brain stimulators. Neurostimulators are used to stimulate the Vagus nerve, for example, to treat epilepsy, obesity and depression. Brain stimulators are pacemaker-like devices and include electrodes implanted deep into the brain for sensing the onset of the seizure and also providing electrical stimulation to brain tissue to prevent the seizure from actually occurring. 10C shows a cardiac pacemaker which is well-known in the art. 10D includes the family of left ventricular assist devices (LVAD's), and artificial hearts, including the recently introduced artificial heart known as the Abiocor. 10E includes an entire family of drug pumps which can be used for dispensing of insulin, chemotherapy drugs, pain medications and the like. 10F includes a variety of bone growth stimulators for rapid healing of fractures. 10G includes urinary incontinence devices. 10H includes the family of pain relief spinal cord stimulators and anti-tremor stimulators. 10H also includes an entire family of other types of neurostimulators used to block pain. 10I includes a family of implantable cardioverter defibrillators (ICD) devices and also includes the family of congestive heart failure devices (CHF). This is also known in the art as cardio resynchronization therapy devices, otherwise known as CRT devices.

Figure 2:
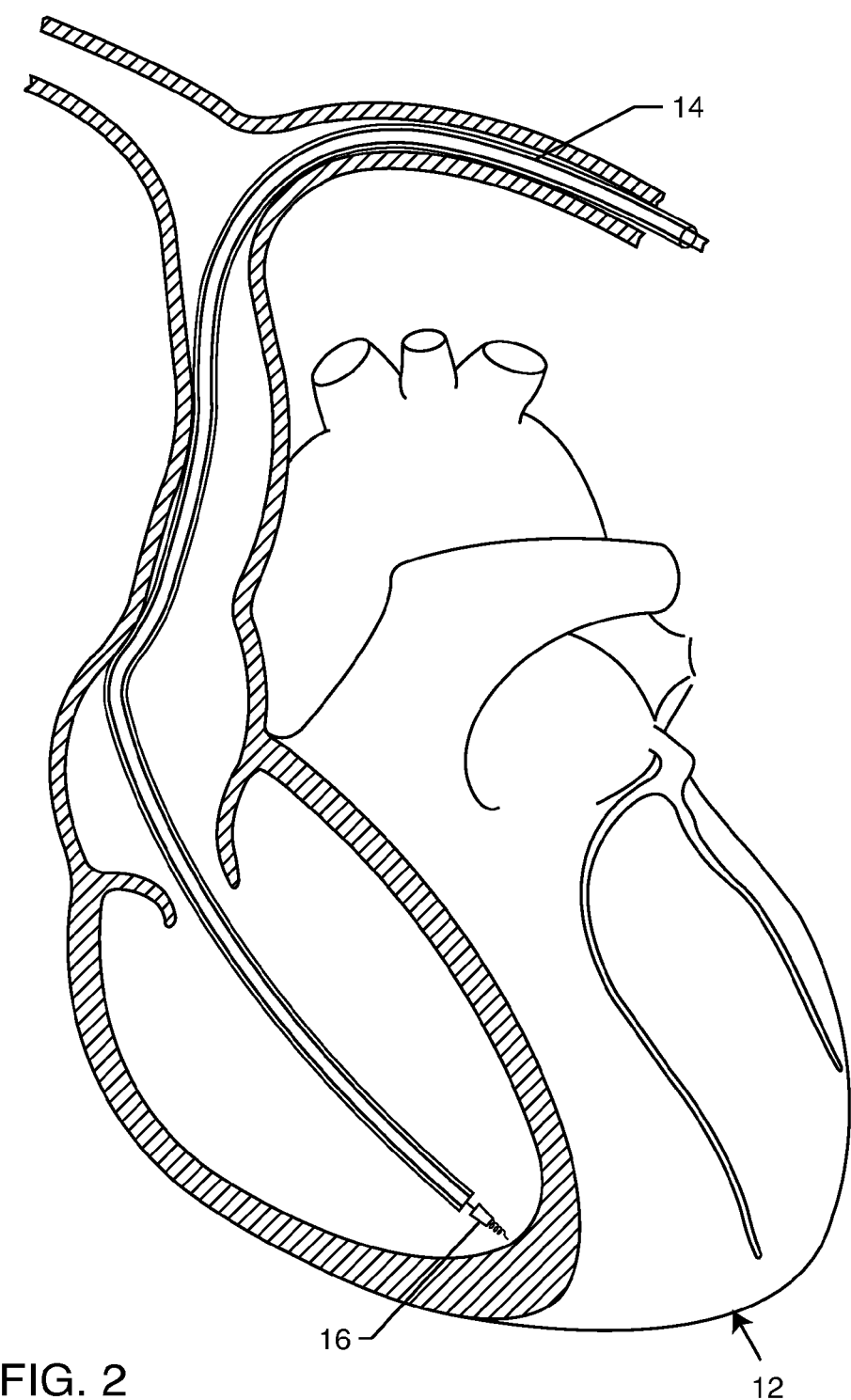
FIG. 2 is a schematic illustration of a human heart with an implanted medical electrical lead.

FIG. 2 is a schematic illustration of a human heart 12 with an implanted medical electrical lead 14. The medical electrical lead 14 includes an electrical or electronic component 16 in series with the distal electrode(s). Once the medical electrical lead 14 is in the desired location, it is typically attached to body tissue with a helical tip (active) or even passive fixation electrode(s).

Figures 3, 3A:
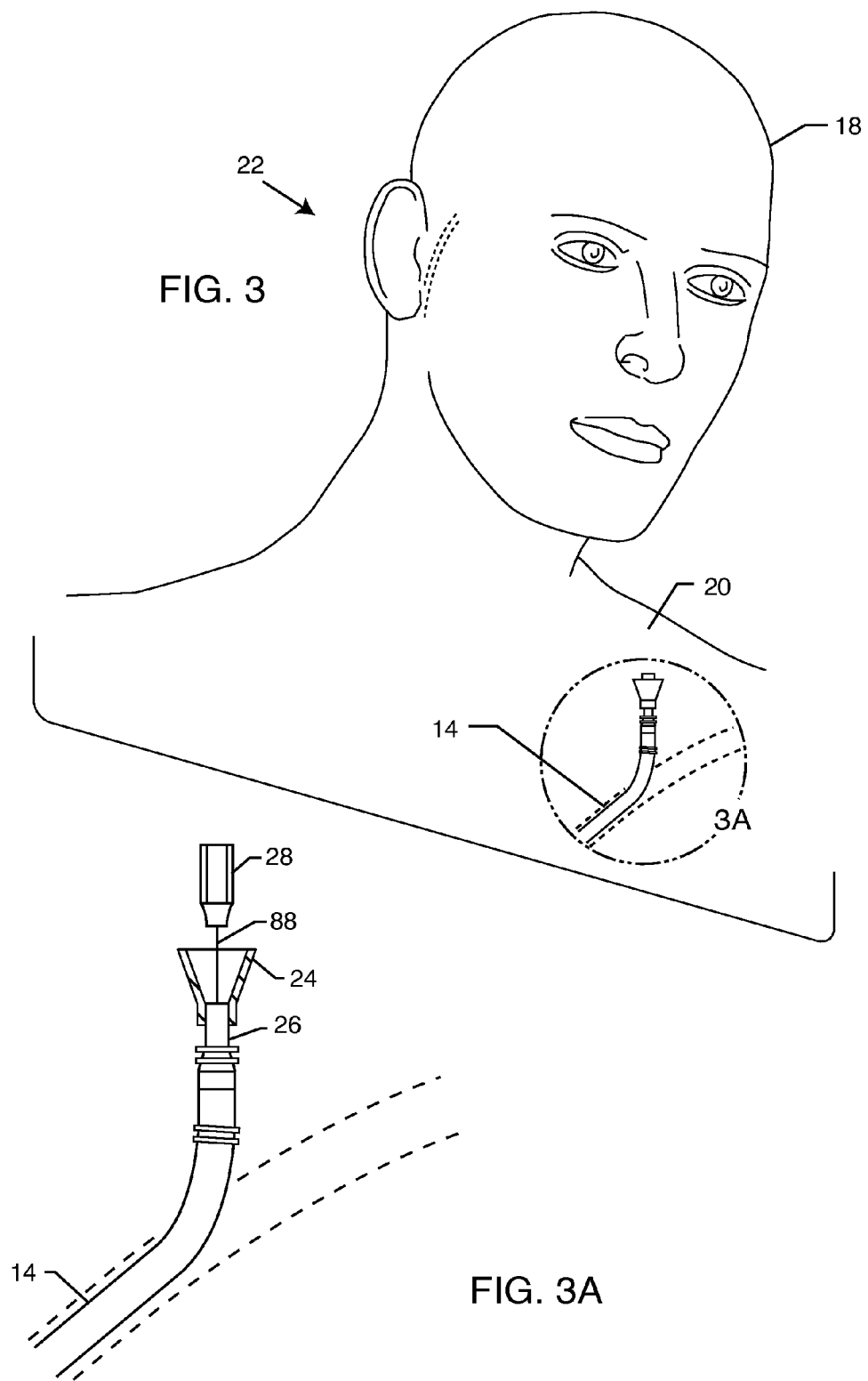
FIG. 3 is an outline illustration of the head and left pectoral region of a patient undergoing implantation of a medical electrical lead.
FIG. 3A is an enlarged view of area 3A in FIG. 3.

FIG. 3 is an outline illustration of the head 18 and left pectoral 20 region of a patient 22 undergoing implantation of a medical electrical lead 14. FIG. 3A is an enlarged view of area 3A in FIG. 3. The medical electrical lead 14 is implanted through a venous access in the left pectoral region of the patient and delivered through the veins and into the heart using an introducer 24, connector pin 26, and stylet knob 28.

FIG. 4 is a general diagram of a unipolar active implantable medical device 10. The AIMD housing 30 is typically titanium, ceramic, stainless steel or the like. Inside of the device housing 30 are the AIMD electronic circuits. Usually AIMDs include a battery, but that is not always the case. A unipolar lead 32 is routed from the AIMD 10 to a distal point 34 where it is embedded in or affixed to body tissue. In the case of a spinal cord stimulator 10H, the distal electrode 34 could be in the spinal cord. In the case of a deep brain stimulator 10B, the distal electrode 34 would be placed deep into the brain, etc. In the case of a cardiac pacemaker 10C, the distal electrode 34 would typically be placed in the cardiac right ventricle.

FIG. 5 is very similar to FIG. 4 except that it is a bipolar system. In this case, the electrical simulation and sensing may be between the two distal electrodes 34 and 34'. In the case of a cardiac pacemaker 10C, this would be known as a bipolar lead wire system with one of the electrodes known as the distal tip electrode 36 and the other electrode which would float in the blood pool known as the ring electrode 38 (see FIG. 6). In contrast, the electrical tissue simulation and sensing path in FIG. 4 is between the distal electrode 34 through body tissue to the conductive housing 30 of the implantable medical device 10 (the bipolar system of FIG. 5 can be typically programmed into the unipolar mode shown in FIG. 4).

FIG. 6 illustrates a bipolar lead wire system with a distal tip electrode 36 and ring electrode 38 typically as used in a cardiac pacemaker 10C.

In all of these applications, a patient exposed to the fields of an MRI scanner or other powerful emitter used during a medical diagnostic procedure, could have currents induced in the lead wire 32 and, in turn, can cause heating by $I^2R$ losses in the lead wire 32 or by heating caused by current flowing in body tissue. If these currents become excessive, the associated heating can cause damage or even destructive ablation to body tissue.

The distal tip electrode 36 is designed to be implanted into or affixed to the actual endocardial tissue of the heart. The ring electrode 38 is designed to float in the blood pool. Because the blood is flowing and is thermally conductive, the ring electrode 38 structure is substantially cooled. In theory, the ring electrode 38 could also touch the myocardial or tribicular tissue and become encapsulated. Electrodes 36 and/or 38, encapsulated, are thermally insulated by surrounding body tissue and can readily heat up due to the RF pulse currents of an MRI field.

FIG. 7 illustrates a single chamber bipolar cardiac pacemaker lead wire showing the distal tip electrode 36 and the distal ring electrode 38. This is a coaxial wound system where the ring electrode lead wire 40 is wrapped around the tip electrode lead wire 42. There are other types of pacemaker lead wire systems in which these two leads lay parallel to one another (known as a bifilar lead system).

FIG. 8 is a schematic illustration of the area 8-8 in FIG. 7. In the area of the distal tip electrode 36 and ring electrode 38, bandstop filter 44 has been placed in series with the tip electrode lead wire 42. The bandstop filter 44 consists of a passive component inductor L in parallel with a capacitor C which is designed to be resonant at an MRI pulsed RF frequency. The resistive losses $R_C$ and $R_L$ of the capacitor and the inductor are carefully controlled such that the bandstop filter 44 has a resulting 3 dB bandwidth to achieve substantial attenuation in the range of MRI RF pulsed frequencies. Accordingly, at MRI pulsed frequencies, a very high impedance is presented thereby reducing the flow of undesirable RF current into body tissue. A bandstop filter 44 could also be placed in series with the ring electrode lead wire 40. The bandstop filter 44 shown is exemplary of any type of passive component network (any combination of inductors, resistors or capacitors) that could be used in the present invention. An electronic switch, a MEMS switch as taught by U.S. Pat. No. 6,944,489 the contents of which are hereby incorporated by reference, a diode array, a multiplexer or any combination thereof, could also advantageously be used with or instead of the bandstop filter 44.

Referring once again to FIG. 8, it is important that the implanted bandstop filter have a high insulation resistance (IR) between points "a" and "b", which are external to the electronic element 44. In this case, the bandstop filter 44 would provide a high impedance at resonance (above 1000 ohms) to reduce the flow of RF currents induced in the lead into body tissue. However, if both ends of the bandstop filter 44 were exposed to ionic containing fluids (i.e. body fluid), then external conduction paths would occur. Experiments by the inventors have shown that a parallel resistance of 80 ohms could result, which would significantly and undesirably reduce the impedance of the bandstop filter 44 at resonance. This parallel IR is shown in FIGS. 8 and 9 as $R_{FL}$ which represents the conduction through body fluid which would occur from end to end (points a to b) if the bandstop filter 44 were not properly insulated and isolated. For a typical bandstop filter, let's assume that its impedance at resonance at 64 MHz was 2000 ohms. If it undesirably had ionic fluids disposed to its external contacts at points a and b, this would mean that an 80 ohm insulation resistance now appears in parallel with the 2000 ohm impedance. Using the parallel resistance $R_P$ formula wherein $R_P=(R_1R_2)/(R_1+R_2)=(80)(2000)/(2000+80)=76.9$ ohms. This would be disastrous for the operation of the bandstop filter. Instead of presenting 2000 ohms at resonance to the MRI pulsed frequency, it would present only 76.9 ohms. This would result in a great deal of RF current flowing through the distal electrode into body tissue which is highly undesirable. It is a feature of the present invention that insulating seals and/or insulating conformal coatings be provided such that this low value of parallel insulation resistance does not occur in parallel with the electronic circuit element. The electronic circuit element of the present invention is not limited to just L-C parallel resonant bandstop filters. It is equally important for electronic switches, MEMS switches, pin diodes, L-C trap filters, low pass filters, diode arrays, electronic multiplexers, or any other type of electronic circuit wherein a high insulation resistance is needed from one end of it to the other end of it, as described as points a and b in FIGS. 8 and 9.

FIG. 9 is very similar to FIG. 8 except that the electronic device 44, in this case, is an electronic switch 45 which is shown in the open position. The electronic switch 45 can actually consist of a pin diode, a MEMS switch, an electronic switch or even a diode array. It is shown in the open position indicating that it's in the MRI compatible position. In other words, MRI RF currents induced onto lead 42 would be unable to flow through distal electrode 36 into body tissue and potentially damage said body tissues. However, if the electronic module casing 44 is not properly insulated and isolated in accordance with the present invention, an undesirable parallel circuit path $R_{FL}$ would exist. As previously mentioned, experiments have shown that this parallel path through body tissues may be as low as 80 ohms measured from points a and b at each end of the electronic module 44. This is extremely undesirable. For example, in the case of an electronic switch as illustrated in FIG. 9, the lead-to-tissue impedance with the switch open would typically be several hundreds of thousands of ohms or higher. It would be very undesirable to have this shunted by 80 ohms through body fluid as significant energy would flow around the switch and into said sensitive body tissue. The present invention describes methods of isolating and insulating points a and b from each other so that this cannot occur.

FIG. 10 illustrates an exemplary lead 14 which embodies a lead body 46, a coaxial conductor 48 for the ring electrode 38 and coaxial conductor 42 for the tip (active fixation helix) electrode 36, a collar 50, and the translatable casing 52 which houses electronic components. The translatable casing 52 includes a pin 54 and a pin 56. The pin 54 is electrically and mechanically connected to the tip electrode lead wire conductor 42 and the pin 56 is attached to the translatable seal assembly 58 which is also connected to a distal helix electrode 36. The distal helix electrode 36 is also known as an active fixation electrode. The pin 54, the casing 52, the pin 56 and the translatable seal structure 58 all form what is defined herein as a casing subassembly 60. This is further illustrated in FIG. 11, which shows an inductor L and a capacitor C inside casing 52, which are physically disposed in series, but are electronically connected in parallel to form an L-C resonant bandstop filter 44. This is further described in U.S. 2010/0100164, which is incorporated herein by reference.

Referring once again to FIG. 10, there will typically be a laser weld (not shown) electrically and mechanically connecting the tip conductor 42 to casing 52 terminal pin 54. There is also a laser weld 62 connecting the casing pin 56 to a weld sleeve 64 of the translatable seal assembly 58. The weld sleeve 64 may be attached to the pin 56 in any known technique including laser welding, bonding, crimping, adhering, other forms of welding, or any other suitable method. The weld sleeve 64 is typically laser welded to the helix electrode 36. During transvenous insertion, the active fixation helix tip 36 is retracted (as shown) so that it will not stab or poke into body tissues during lead insertion. When the physician has positioned it in the desirable location (perhaps inside the cardiac right ventricle), then the physician takes a special tool and twists the proximal end of lead body 46 causes the entire conductor 42 and casing subassembly 60 to rotate. As the distal helix electrode 36 rotates, it engages a guide 66 which causes the helix 36 to extend and screw into body tissue. The guide 66 may be formed as part of the collar 50 and engages the tip electrode 36 when the tip conductor 42 is rotated. The rotation causes the helical tip electrode 36 to rotate within the collar 50 and thereby translate in a forward manner. At the same time the tip electrode 36 is advancing relative to the collar 50, it is engaging with body tissue by being screwed directly into the tissue forming an attachment. The tip electrode 36 can be rotated in the opposite direction by the tip conductor 42 and thereby disengaged from the tissue for removal and/or reattachment at a different location. This is a method of active affixation which is well known in the art.

FIG. 11 is generally taken from section 11-11 from FIG. 10. Shown is the interior of the translatable casing 52 illustrating bandstop filter components L and C. Shown are terminal pins 54 and 56 which extend in non-conductive relationship with the translatable casing 52. Hermetic seals 43 and 43' are shown which form a hermetic seal between the pins 54 and 56 and the translatable casing 52. This protects the L and C (or other electronic components) from intrusion of body fluids. It is well known in the art that intrusion of moisture, body fluids or other contaminants can cause electronic circuits to short out. It is not an absolute requirement that the translatable casing 52 be hermetically sealed. Electronic components, such as inductor L and capacitor C components, could be utilized that are inherently non-toxic and biocompatible. Components for direct body fluid exposure are described in U.S. Pat. No. 7,535,693 the contents of which are hereby incorporated by reference.

Referring once again to FIG. 11 the present invention is applicable to any type of active or electronic circuits that may be disposed in a translatable electronic casing 52. The flexible seal 68 of FIG. 10 slides against the interior of the collar 50 thereby preventing the entrance of ionic body fluids into the inside of the lead body 46. The seal 68 may be bonded, molded, adhered, or formed onto the weld sleeve 64 by any suitable means. The seal 68 can be formed in a multitude of ways appreciated by those skilled in the art, such as multiple wipers, o-rings, thin disks or sheets, and various molded profiles (see FIGS. 16-20).

There is a secondary optional O-ring seal 70 as shown in FIG. 10. The O-ring seal 70 is disposed between the inside diameter of the lead collar 50 and the outside diameter of the electronic component casing 52. The purpose of seal 68 and the O-ring seal 70 is to ensure that ionic body fluids cannot be disposed across the important electrical path between pins 54 and 56. Ionic body fluids could represent a parallel path as low as 80 ohms. Over time, due to bulk permeability, body fluids will penetrate into the interior of the lead body 46. However, this is an osmotic type of action. The resulting fluids that would occur over long periods of time inside the lead body 46 would be distilled and free of ionic contaminants (de-ionized). This means that they would be less conductive of high frequency electrical signals from one end to the other of the electronic component casing 52. The presence of optional O-ring 70 is desirable in that it also presents a high impedance to such a parallel circuit path. The casing 52 may also have a conformal insulative coating (not shown) for further electrically isolating terminals 54 and 56 such that a parallel path through body fluid is further impeded. The insulative coating may be formed from any suitable material, such as a dielectric material, including, but not limited to parylene, ETFE, PTFE, polyamide, polyurethane and silicone. It will be understood that the exemplary embodiment of FIG. 10 may work with or without such coatings.

FIG. 12 is very similar to FIG. 10 except that the seal 68 is disposed on the proximal end of the electronic casing 52 and subassembly 60. In this case, the seal 68 is only to prevent the intrusion of ionic containing body fluids into the interior of lead body 46. In this case, a conformal coating 72 is disposed over the exterior of the electronic casing 52 and all the way over the pin 54 and even over a portion of a conductive drive shaft 74. The conformal coating 72 may be a dielectric material for electrical isolation and/or also aid in reducing friction. The conformal coating 72 may also be a dielectric ceramic coating that can be applied in a multitude of ways, such as by sputtering, chemical vapor deposition, physical vapor deposition, or dipping in a chemical solution. The conformal coating 72 may also be made of a variety of materials sufficient to provide insulation, such as alumina. In another exemplary embodiment and to provide further electrical isolation, the casing 52 can also be manufactured as a ceramic tube, and also from materials such as alumina. It is to be understood that the ceramic tube casing 52 can be used with or without the conformal coating 72.

In FIG. 12, the lead tip conductor 42, the electronic casing assembly 60 and the distal helix 36 are shown in the retracted position. As the helix is extended, the conformal coating 72 on the inside diameter of seal 68 will slide back and forth as it is part of the drive shaft 74. This provides a high degree of electrical resistance or isolation between the terminal pins 54 and 56 such that undesirable currents do not flow through body fluids from end to end outside of the electronic component casing 52. Seal supports 76 abut the seal 68 on both ends and fix the seal 68 in place. The seal supports 76 can be made from a range of materials, including but not limited to a polymer, polyurethane, metal, elastomer, ceramic, composite or any other suitable material.

FIG. 13 is taken from section 13-13 of FIG. 12, and shows an alternative configuration of components at the proximal end of the casing subassembly 60, wherein the pin 54 has been elongated to obviate the need for the drive shaft 74 illustrated in FIG. 12. As illustrated, the lead tip conductor 42 was conductively attached directly to the elongated pin 54. Further, the conformal coating 72 extends from an area at least partially coating the translatable casing 52, over an end of the translatable casing and over the pin 54 through the attachment of the lead tip conductor 42.

Figure 14:
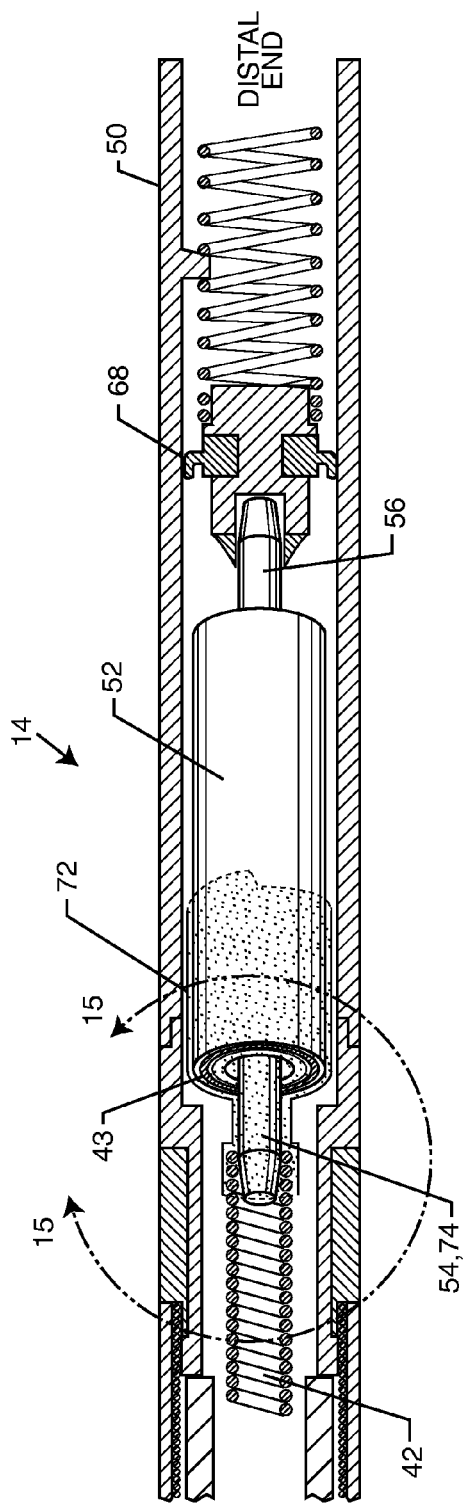
FIG. 14 is a sectional view similar to FIGS. 10 and 12 of another exemplary medical electrical lead embodying the present invention.

FIG. 14 is similar to FIGS. 10 and 12, and illustrates an alternative embodiment wherein a distal seal 68 is combined with a partial conformal coating 72. The partial conformal coating 72 is disposed on at least a portion of the electronic component casing 52, over the left hand hermetic seal 43 of the electronic component casing 52 and also over the pin 54/drive shaft 74 that's connected to the tip conductor 42.

Figure 15:
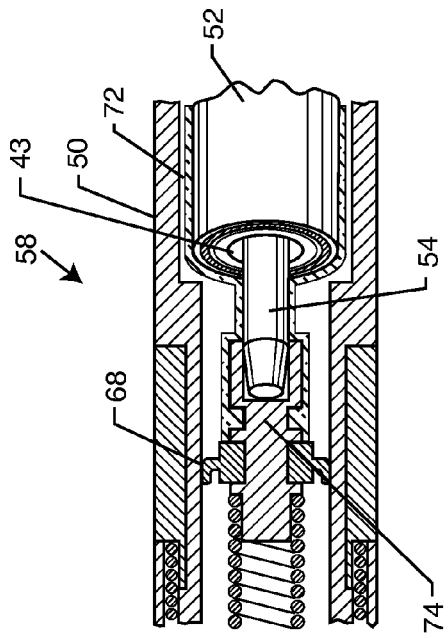
FIG. 15 is a sectional of the area illustrated by line 15-15 in FIG. 14, showing an alternative configuration including a proximal second seal.

FIG. 15 is taken from the area indicated by line 15-15 of FIG. 14 and shows an alternative configuration wherein the seal assembly 58 is proximal to the electronic component casing 52. In this case, electrical isolation protection between pins 54 and 56 is provided entirely by the conformal coating 72 which extends over at least a portion of the electronic casing 52 including the pin 54 and a portion of the drive shaft assembly to the right of the drive shaft 74 and to the seal 68.

Figure 16:
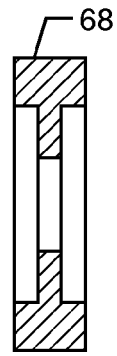
FIGS. 16-20 are sectional views of exemplary seals used in a medical electrical lead embodying the present invention.
Figure 17:
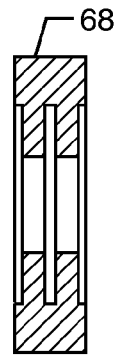
Figure 18:
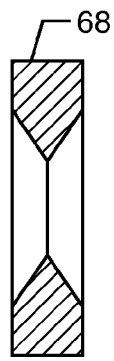
Figure 19:
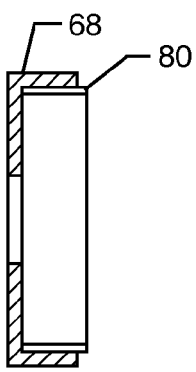
Figure 20:
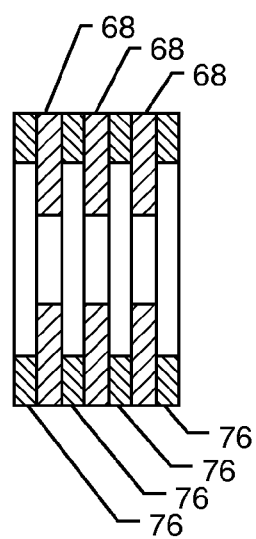

FIGS. 16 through 20 describe alternative seal embodiments 68 to those previously illustrated in FIGS. 10, 12, 13, 14 15. The seal 68 may be comprised of one contact section as illustrated in FIG. 16, or from a multitude of surfaces as shown in FIGS. 17 and 20. FIG. 18 shows the seal 68 narrowing to a smaller contact area. This may help reduce torsional and frictional loads during implanting. FIG. 19 illustrates the seal 68 made from a thin sheet then formed over a support ring 80. FIG. 20 illustrates the multitude of seals 68 sandwiched between a multitude of seal supports 76. It will be appreciated that a multitude of seal 68 and seal support 76 combinations can be made.

Figure 21:
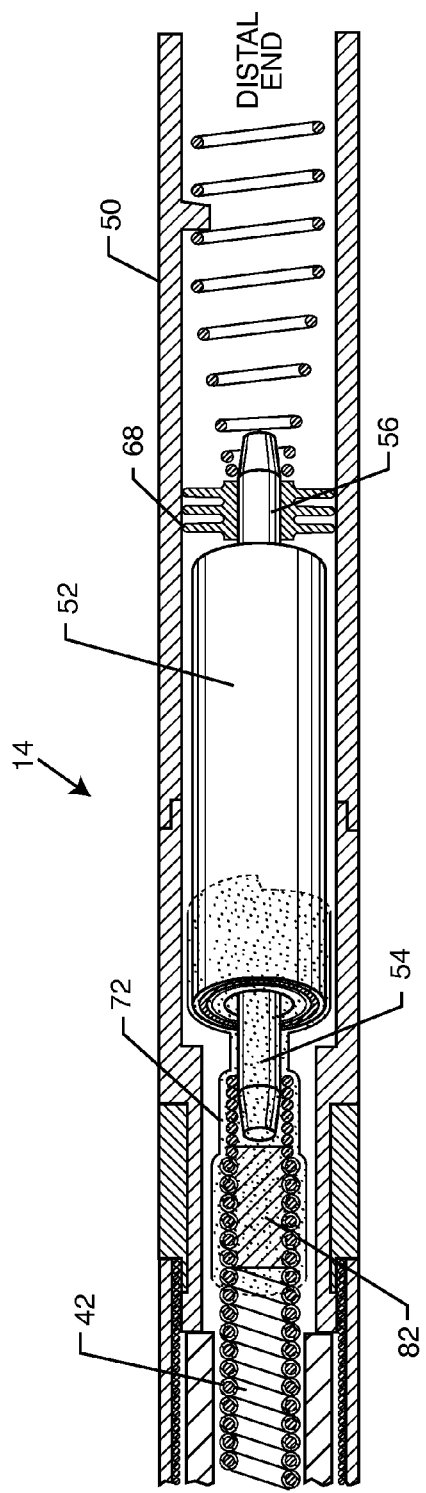
FIG. 21 is a sectional view similar to FIGS. 10, 12 and 14, of another exemplary medical electrical lead embodying the present invention.

FIG. 21 illustrates a multiple redundant seal 68 to provide further protection. Also shown is an optional conformal coating 72 which would back up or provide redundant electrical isolation between the pins 54 and 56. A backfill material 82 may be placed within the tip conductor 42 abutting the pin 54. The backfill material 82 may be an insulator, or also a silicone medical adhesive or any other suitable adhesive.

Figure 22:
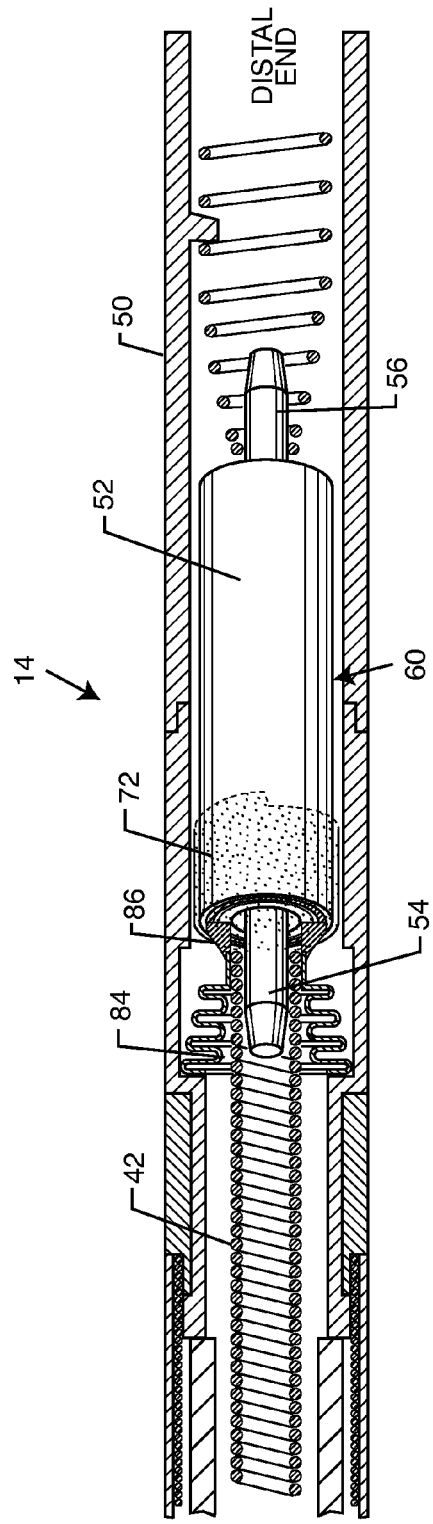
FIG. 22 is a sectional view similar to FIG. 21, of yet another exemplary medical electrical lead embodying the present invention.

FIG. 22 illustrates a novel bellows assembly wherein a bellows 84 is attached near the proximal end of the casing 52. The bellows 84 is attached to the collar 50 and also to the casing 52 at a laser weld 86 or other suitable attachment means. The bellows 84 is expandable and collapsible. The bellows 84 may also be pre-spiraled in either a counter clockwise or clock-wise direction to ease twisting stresses on the bellows 84 when the inner casing assembly 60 is rotated and translated. The bellows 84 may be manufactured from an electrically non-conductive material. A conformal coating 72 may also cover the bellows 84 and the casing 52, or a portion of the bellows 84 and casing 52.

Figure 23:
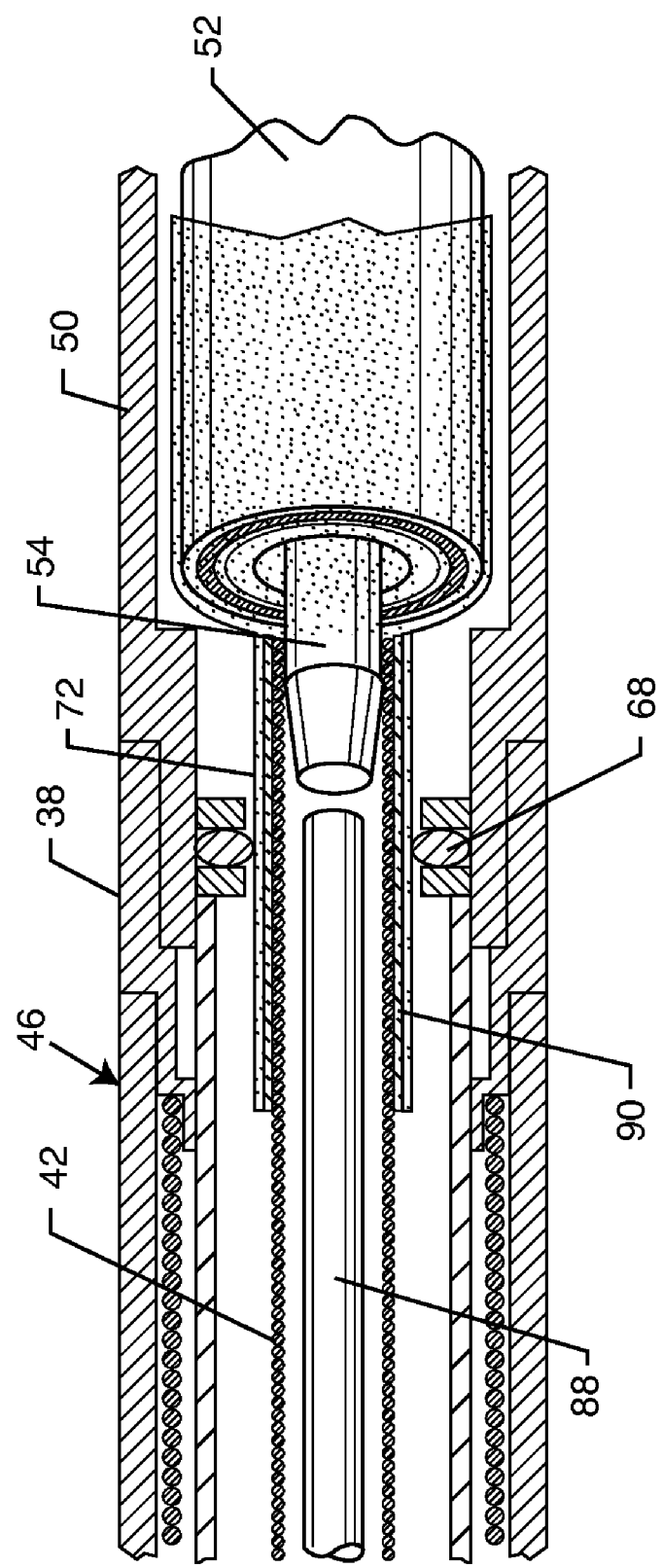
FIG. 23 is similar to FIG. 13, and illustrates a hollow stylet-receiving drive shaft.

Referring once again to FIG. 12, one can see that there is a drive shaft 74, which is connected to pin 54. The proximal end of this drive shaft is laser welded or otherwise connected (not shown) to the distal tip conductor 42 of lead body 46. The presence of the solid drive shaft 74 and the electronic casing 52, which may contain a bandstop filter or other electrical components, prevents the stylet 28, as illustrated in FIG. 3A, from extending all the way to the distal end, which would be as close as possible to electronic casing 52. FIG. 23 illustrates a hollow stylet-receiving drive shaft 90 in the form of a rigid tube. This makes electrical and mechanical contact with lead conductor 42 and also the pin 54 of electronic housing 52. It is hollow for reception of the stylet guide wire 88 as shown. This is also accomplished as shown in FIG. 10 by direct contact or direct connection of conductor 42 to the outside of pin 54 leaving its interior hollow. Therefore the structure of FIG. 10 may also receive the stylet guide wire 88 as illustrated in FIG. 23. In FIG. 23, this metal tube 90 is swaged onto the outside of the pin 54 and lead conductor 42. By having the stylet extend into the distal tip of lead conductor 42, this increases the ability of the physician to control the lead tip during lead placement. The strength of the swage can be further increased by a 360 degree weld to the lead conductor 42 (not shown). The hollow drive shaft 90 can also be laser welded to pin 54 along with conductor 42. In other words, in a preferred embodiment, the weld encapsulates both the hollow tube and the lead conductor coil 42. In summary, the hollow drive shaft 90 allows for stylet passage into the rigid tip of lead for improved handling characteristics during implantation.

From the foregoing, it will be appreciated that the present invention relates to a lead body adapted for in-vivo implantation in a living subject, said lead body comprising a proximal end configured for electrical and mechanical connection to a therapy delivery or monitoring device, and a distal end which is connected to a translatable electrode in contact with body tissues. The distal end of the lead body encompasses a collar in which a casing is enclosed. The casing includes electronic components which can either be active or passive. In a preferred embodiment, the casing includes a passive inductor and capacitor element configured to form a parallel resonant L-C bandstop filter. The casing is translatable within the collar, which causes a distal helix electrode to rotate and literally be screwed into body tissue. The helix electrode is also known as an active fixation electrode. The casing is part of a casing assembly which includes a seal which is disposed between the casing assembly and the collar whereby the seal prevents passage of ionic body fluids in the living subject into the lead body fluid distal end. Conformal coatings can be placed over the translatable casing so that high resistance path is provided from one end of the active or passive electronic circuit to the other. The active or passive electronic circuit can include L-C bandstop filters, L-C trap filters, low pass filters, passive or active electronic switches, MEMS switches, pin diode switches, non-linear circuit elements, such as diodes and the like. The conformal coating may be a dielectric material for electrical isolation and/or also aid in reducing friction.

Although several embodiments have been described in detail for purposes of illustration, various modifications may be made to each without departing from the scope and spirit of the invention.

What is claimed is:

1. An implantable medical lead, comprising:
   a) a lead body adapted for in-vivo implantation in a living subject, the lead body comprising at least one electrical conductor extending from a conductor distal end to a conductor proximal end that is configured to be electrically connectable to a therapy delivery or a monitoring device;
   b) a collar disposed at the distal end of the lead body, the collar comprising a proximal collar end extending to an open distal collar end;
   c) a casing extending from a proximal casing end to a distal casing end, wherein the casing is disposed within the collar and translatable along a longitudinal axis thereof;
   d) at least one electronic component disposed within the casing, but electrically insulated therefrom, wherein the electronic component is electrically coupled to the distal end of the electrical conductor;
   e) an electrode electrically connected to the electronic component at the distal casing end; and
   f) a seal supported by at least one of the collar and the casing and extending to the other of the collar and the casing so as to substantially prevent passage of fluid to the proximal casing end from the open distal collar end,
   g) wherein the at least one electrical conductor, the casing and the electrode are axially translatable along the collar to extend the electrode distally beyond the open distal collar end and to alternatively retract the electrode proximally into the collar as a contact location of the seal between an inner surface of the collar and an outer surface of the casing changes upon such axial proximal and distal translation thereof.

2. The lead of claim 1, wherein the seal is supported at at least one of a distal end, a proximal end, or along a middle of the casing.

3. The lead of claim 1, wherein the seal is supported by the collar, fixed relative to the casing.

4. The lead of claim 1, wherein the seal is supported by the casing, fixed relative to the collar.

5. The lead of claim 1, wherein the at least one electrical component is selected from the group consisting of a bandstop filter, an electronic switch, a MEMS switch, a diode array, a multiplexer, a PIN diode, a capacitor, a resister, an inductor, and any combination thereof.

6. The lead of claim 1, including an insulative conformal coating disposed about at least a portion of the casing.

7. The lead of claim 6, wherein the conformal coating comprises a dielectric ceramic coating.

8. The lead of claim 6, wherein the conformal coating is characterized as having been applied by a process selected from the group consisting of sputtering, chemical vapor deposition, physical vapor deposition, dipping in a chemical solution, and by applying a chemical solution.

9. The lead of claim 6, wherein the conformal coating comprises alumina or parylene.

10. The lead of claim 1, wherein the casing comprises a dielectric ceramic coating.

11. The lead of claim 1, wherein the casing comprises alumina.

12. The lead of claim 1, wherein the casing comprises a distal pin and a proximal pin, both pins being electrically insulated from the casing, and wherein the at least one electrical conductor is attached to the proximal pin and the electrode is attached to the distal pin.

13. The lead of claim 12, including a drive shaft connected to a distal end of the at least one electrical conductor.

14. The lead of claim 13, wherein the drive shaft comprises a hollow stylet-receiving drive shaft.

15. The lead of claim 14, wherein the hollow stylet-receiving drive shaft comprises a rigid tube surrounding at least a portion of the proximal pin of the casing.

16. The lead of claim 12, including an insulative conformal coating disposed about the proximal pin such that the proximal and distal pins are electrically insulated when surrounded by an ionized fluid.

17. The lead of claim 1, wherein the seal comprises a plurality of seals.

18. The lead of claim 1, wherein the seal is selected from the group consisting of multiple wipers, o-rings, thin disks, and thin sheets.

19. The lead of claim 1, wherein the seal comprises a bellows disposed between the collar and the casing.

20. The lead of claim 19, wherein the bellows is expandable and collapsible.

21. An implantable medical lead, comprising:
 a) a lead body adapted for in-vivo implantation in a living subject, the lead body comprising at least one electrical conductor extending from a conductor distal end to a conductor proximal end that is configured to be electrically connectable to a therapy delivery or a monitoring device;
 b) a collar disposed at the distal end of the lead body, the collar comprising a proximal collar end extending to an open distal collar end;
 c) a casing extending from a proximal casing end to a distal casing end, wherein the casing is disposed within the collar and translatable along a longitudinal axis thereof;
 d) at least one electronic component disposed within the casing, but electrically insulated therefrom, wherein the electronic component is electrically coupled to the distal end of the electrical conductor;
 e) an electrode electrically connected to the electronic component at the distal casing end;
 f) a seal supported by at least one of the collar and the casing and extending to the other of the collar and the casing so as to substantially prevent passage of fluid to the proximal casing end from the open distal collar end; and
 g) an insulative conformal coating disposed about at least a portion of the casing, the at least one electrical conductor, or both
 h) wherein the at least one electrical conductor, the casing and the electrode are axially translatable along the collar to extend the electrode distally beyond the open distal collar end and to alternatively retract the electrode proximally into the collar as a contact location of the seal between an inner surface of the collar and an outer surface of the casing changes upon such axial proximal and distal translation thereof.

22. The lead of claim 21, wherein the seal is fixed relative to the casing or the collar.

23. The lead of claim 21, wherein the seal is selected from the group consisting of a plurality of seals, multiple wipers, o-rings, thin disks, thin sheets, and a bellows disposed between the collar and the casing.

24. The lead of claim 23, wherein the bellows is expandable and collapsible.

25. The lead of claim 21, wherein the at least one electrical component is selected from the group consisting of a band-stop filter, an electronic switch, a MEMS switch, a diode array, a multiplexer, a PIN diode, a capacitor, a resister, an inductor, and any combination thereof.

26. The lead of claim 2 wherein the conformal coating comprises a dielectric ceramic coating comprising alumina characterized as having been applied by a process selected from the group consisting of sputtering, chemical vapor deposition, physical vapor deposition, dipping in a chemical solution and and applying a chemical solution.

27. The lead of claim 21, wherein the insulative conformal coating comprises a dielectric ceramic coating comprising alumina.

28. The lead of claim 21, wherein the casing comprises a distal pin and a proximal pin, both pins being electrically insulated from the casing, and wherein the at least one electrical conductor is attached to the proximal pin and the electrode is attached to the distal pin.

29. The lead of claim 28 wherein the insulative conformal coating is disposed about the proximal pin such that the proximal and distal pins are electrically insulated when surrounded by an ionized fluid.

30. The lead of claim 29, including a drive shaft connected to a distal end of the at least one electrical conductor.

31. The lead of claim 30, wherein the drive shaft comprises a hollow stylet-receiving drive shaft including a rigid tube surrounding at least a portion of the proximal pin of the casing.

32. An implantable medical lead, comprising:
 a) a lead body adapted for in-vivo implantation in a living subject, the lead body comprising at least one electrical conductor extending from a distal end to a proximal end that is configured to be electrically connectable to a therapy delivery or a monitoring device;
 b) a collar disposed at the distal end of the lead body, the collar comprising a proximal collar end extending to an open distal collar end;
 c) a casing extending from a proximal pin at a proximal casing end to a distal pin at a distal casing end, wherein the casing is disposed within the collar and translatable along a longitudinal axis thereof and wherein the proximal and distal pins are electrically insulated from the casing;
 d) at least one electronic component disposed within the casing, but electrically insulated therefrom, wherein the electronic component is electrically coupled to the electrical conductor at the proximal pin;
 e) an electrode mechanically and electrically coupled to the electronic component at the distal pin; and
 f) a seal disposed between the casing and the collar to substantially prevent passage of fluid to the proximal casing end from the open distal collar end thereof.

33. An implantable medical lead, comprising:
 a) a lead body adapted for in-vivo implantation in a living subject, the lead body comprising at least a first and a second electrical conductors extending from respective first and second distal ends to first and second proximal ends that are configured to be electrically connectable to a therapy delivery or a monitoring device;
 b) a collar disposed at the distal end of the first electrical conductor, the collar comprising a proximal collar end extending to an open distal collar end;
 c) a casing extending from a proximal casing end to a distal casing end, wherein the casing is disposed within the collar and translatable along a longitudinal axis thereof;
 d) at least one electronic component disposed within the casing, but electrically insulated therefrom, wherein the electronic component is electrically coupled to the distal end of the second electrical conductor;

e) an electrode electrically connected to the electronic component at the distal casing end; and f) a seal supported by at least one of the collar and the casing and extending to the other of the collar and the casing so as to substantially prevent passage of fluid to the proximal casing end from the open distal collar end, g) wherein the second electrical conductor, the casing and the electrode are axially translatable along the collar to extend the electrode distally beyond the open distal collar end and to alternatively retract the electrode proximally into the collar as a contact location of the seal between an inner surface of the collar and an outer surface of the casing changes upon such axial proximal and distal translation thereof.

34. An implantable medical lead, comprising:

a) a lead body adapted for in-vivo implantation in a living subject, the lead body comprising at least a first and a second electrical conductors extending from respective first and second distal ends to first and second proximal ends that are configured to be electrically connectable to a therapy delivery or a monitoring device;

b) a collar disposed at the distal end of the first electrical conductor, the collar comprising a proximal collar end extending to an open distal collar end;

c) a casing extending from a proximal casing end to a distal casing end, wherein the casing is disposed within the collar and translatable along a longitudinal axis thereof;

d) at least one electronic component disposed within the casing, but electrically insulated therefrom, wherein the electronic component is electrically coupled to the distal end of the second electrical conductor;

e) an electrode electrically connected to the electronic component at the distal casing end; and f) an annular seal supported by the casing and extending to the collar to substantially prevent passage of fluid to the proximal casing end from the open distal collar end thereof, g) wherein the second electrical conductor, the casing and the electrode are axially translatable along the collar to extend the electrode distally beyond the open distal collar end and to alternatively retract the electrode proximally into the collar as a contact location of the seal against an inner surface of the collar changes upon such axial proximal and distal translation thereof.

35. An implantable medical lead, comprising:

a) a lead body adapted for in-vivo implantation in a living subject, the lead body comprising at least one electrical conductor extending from a conductor distal end to a conductor proximal end that is configured to be electrically connectable to a therapy delivery or a monitoring device;

b) a collar disposed at the distal end of the lead body, the collar comprising a proximal collar end extending to an open distal collar end;

c) a casing extending from a proximal casing end to a distal casing end, wherein the casing is disposed within the collar and translatable along a longitudinal axis thereof;

d) at least one electronic component disposed within the casing, but electrically insulated therefrom, wherein the electronic component is electrically coupled to the distal end of the at least one electrical conductor;

e) an electrode electrically connected to the electronic component at the distal casing end; and f) a seal support connected between the distal casing end and the electrode, the seal support supporting an annular seal extending to the collar to substantially prevent passage of fluid to the proximal casing end from the open distal collar end thereof, g) wherein the at least one electrical conductor, the casing, the seal support including the seal, and the electrode are axially translatable along the collar to extend the electrode distally beyond the open distal collar end and to alternatively retract the electrode proximally into the collar as a contact location of the seal against an inner surface of the collar changes upon such axial proximal and distal translation thereof.

36. The implantable medical lead of claim 35 wherein the collar is electrically connected to a second electrical conductor.

37. An implantable medical lead, comprising:

a) a lead body adapted for in-vivo implantation in a living subject, the lead body comprising at least one electrical conductor extending from a conductor distal ends to a conductor proximal end that is configured to be electrically connectable to a therapy delivery or a monitoring device;

b) a collar disposed at the distal end of the lead body, the collar comprising a proximal collar end extending to an open distal collar end;

c) a casing extending from a proximal casing end to a distal casing end, wherein the casing is disposed within the collar and translatable along a longitudinal axis thereof;

d) at least one electronic component disposed within the casing, but electrically insulated therefrom, wherein the electronic component is electrically coupled to the distal end of the electrical conductor;

e) an electrode electrically connected to the electronic component at the distal casing end;

f) a seal support connected between the distal casing end and the electrode, the seal support supporting a first, annular seal extending to the collar to substantially prevent passage of fluid to the proximal casing end from the open distal collar end thereof; and g) a second seal supported by at least one of the collar and the casing and extending to the other of the collar and the casing so as to substantially prevent passage of fluid to the proximal casing end, h) wherein the at least one electrical conductor, the casing, the seal support including the first seal, and the electrode are axially translatable along the collar to extend the electrode distally beyond the open distal collar end and to alternatively retract the electrode proximally into the collar as a contact location of the first seal against an inner surface of the collar changes and as a contact location of the second seal between the inner surface of the collar and an outer surface of the casing changes upon such axial proximal and distal translation thereof.

38. The implantable medical lead of claim 37 wherein the collar is electrically connected to a second electrical conductor.

* * * * *